United States Patent [19]

Alam

[11] Patent Number: 5,300,440
[45] Date of Patent: Apr. 5, 1994

[54] PROTEIN ASSAY METHOD

[76] Inventor: Aftab Alam, 731 Leland Ave., St. Louis, Mo. 63130

[21] Appl. No.: 862,755
[22] PCT Filed: Jun. 4, 1990
[86] PCT No.: PCT/GB90/00859
    § 371 Date: Jun. 24, 1992
    § 102(e) Date: Jun. 24, 1992
[87] PCT Pub. No.: WO91/19198
    PCT Pub. Date: Dec. 12, 1991

[51] Int. Cl.$^5$ .............................................. G01N 33/00
[52] U.S. Cl. ...................................... 436/86; 436/164
[58] Field of Search ................... 436/86, 164; 422/61, 422/68.1

[56] References Cited

U.S. PATENT DOCUMENTS 4,104,030  8/1978  Hopkins, II et al. ................. 435/18
4,786,605  11/1988 Mauck et al. ........................ 436/86

OTHER PUBLICATIONS

Markwell et al. Analytical Biochemistry, vol. 87, pp. 206-210, 1978.
Legler et al. Analytical Biochemistry, vol. 150, pp. 278-287, 1985.
Blümel et al. Analytical Biochemistry, vol. 76, pp. 524-529, 1976.
Harrington Analytical Biochemistry, vol. 186, pp. 285-287, 1990.
Rodriguez-Vico et al. Analytical Biochemistry, vol. 183, pp. 275-278, 1989.
Ledoux et al. Analytical Biochemistry, vol. 157, pp. 28-31, 1986.
Larson et al. Analytical Biochemistry, vol, 155, pp. 243-248, 1986.
Lowry et al. J. Biological Chemistry, vol. 193, pp. 265-275, 1951.

Primary Examiner—James C. Housel
Assistant Examiner—Maureen M. Wallenhorst
Attorney, Agent, or Firm—Nixon & Vanderhye

[57] ABSTRACT

A method for protein assay is a modified Lowry method in which a Step 1 reaction between a copper-containing alkaline solution and a protein solution takes place at high alkali concentration. The Step 2 reaction the products of Step 1 and Folin reagent commences at a pH of 11 and 12 in order to produce rapidly the colored species on the basis of which a maximum optical density is reached in a relatively short time and remains constant for a sufficient period to enable the required number of optical density determinations to be made.

10 Claims, 12 Drawing Sheets

PROTEIN ASSAY METHOD

This invention relates to a protein assay method and a kit in which the amount of protein present in a solution is determined by measuring the optical density of a coloured material produced as a result of reactions between the protein, an alkaline copper solution and Folin reagent.

BACKGROUND OF THE INVENTION

There are several methods for determination of protein quantity in samples. These include use of colour-changing dyes, such as Orange G, Bromo cresol green, Pyrocatechol Violet-Molybdenum complex, etc. These dyes, when bound with protein, change colour proportional to the amount of protein present in the samples. These methods are generally not very sensitive. A more sensitive dye-binding technique using Coomassie Brilliant Blue G-200 is adversely affected by the presence of detergents in sample and also suffers from wide protein-to-protein variation (Bradford, M., Anal. Biochem., 72 248–254, 1976 and U.S. Pat. No. 4,023,933).

A variety of turbidimetric methods are also known in which protein is precipitated by various agents. These methods also suffer from lack of sensitivity, specificity and interference with detergents.

The most widely used procedures for protein determination involve the well-known reaction of protein in alkaline medium with Cupric ions yielding highly reactive cuprous ions. A method using alkaline copper was first developed by Lowry et al (Lowry, Oh. H., Rosebrough, N. J., Farr, A. L., and Randall, R. J., J. Biol. Chem. 193, 265–275, 1951) ("the Lowry method") in which protein reaction with buffered alkaline copper was coupled with Folin phenol reagent (phosphomolybdic/phosphotungstic acid), hereinafter referred to as Folin. It is believed that protein reacts with alkaline copper and produces cuprous ions and this, in turn, reduces the Folin to the characteristic blue reaction colour.

The Lowry method suffers from many disadvantages. The most serious disadvantage is the rigidity of the method. The Lowry method requires precisely-timed additions of reagent, immediate vortexing and prolonged incubation. Furthermore, the Lowry method also suffers from poor reproducibility and interference from a number of commonly used laboratory agents. Attempts to simplify the Lowry method have not, so far, been successful. Consequently, a need exists for a more flexible and rapid method for determination of protein.

In a recent modification, Smith et al (Anal. Biochem. 150, 76–85, 1985) combined the reaction of protein with alkaline copper with bicinchoninic acid. Although Smith et al's method has several advantages over the Lowry method, it suffers from lack of end-point in the reaction. The colour yield of the reaction continues to increase at a rate of 2–3% every ten minutes. Consequently, this method is not very accurate and the problem is compounded if a large number of samples are analysed in a single batch. In addition, Smith et al's method, using bicinchoninic acid, is a slow reaction requiring heating and a prolonged incubation period, which makes the method time-consuming.

SUMMARY OF THE INVENTION

According to the present invention, there is provided a method which comprises the following steps:
(a) contacting together a protein-containing solution and an alkaline copper solution, the alkali concentration in the copper solution being at least 0.2N;
(b) contacting together the product of Step (a) above and Folin reagent, the amount of Folin reagent being such that the initial pH of the resultant solution is from 11 to 12; and
(c) allowing the products of Step (b) above to incubate at ambient temperature until the optical density of the solution reaches a maximum value and reading this maximum optical density in order to determine the amount of protein in said protein-containing solution.

The present invention also provides a kit for use in assaying protein, the kit comprising:
an alkaline solution in which the concentration of alkali is at least 0.2N;
a solution of a cupric salt; and
a solution of Folin reagent.

A method in accordance with the present invention is a two-step procedure in which no incubation period is required after the performance of the first step. As far as the second step is concerned, maximum optical density may be reached in as little as 10 minutes and this maximum optical density may be maintained over a period of, for instance, 10 to 40 minutes during which the optical density measurement may be taken. In the Lowry method, it is necessary to incubate for at least 10 minutes the products of the first step of the method and then wait for at least 30 or 40 minutes before making the optical density measurement after the second step of the method.

It had previously been considered that the second step of the Lowry method has to be carried out at a pH of about 10 and that the reaction solution should be maintained at this pH rather than being allowed to move downwardly, which would otherwise happen as the reaction proceeds and promotes decomposition of the coloured material in the solution. Contrary to accepted practice for very many years, it has now been surprisingly discovered that a quite different approach to the pH of the reaction solution enables highly reproducible results to be obtained much more quickly than with the traditional Lowry method. The key to the discovery is that, in Step 2 of the method, relatively very rapid reaction takes place at a pH of between 11 and 12, preferably between 11.4 and 11.9, more preferably between 11.5 and 11.8 and most preferably between 11.6 and 11.7. At the same time, the pH may be allowed to move downwardly rather than being maintained at this relatively high level. Movement of the pH downwardly means that the coloured species produced are relatively stable. Accordingly, a maximum optical density can be reached rapidly and held at the maximum level for a considerable period, more than sufficient to allow optical density measurements to be taken.

A relatively high alkaline concentration is used in Step 1 of the reaction. This has the added advantage that Step 1 of the reaction proceeds much more quickly than the first step of the conventional Lowry method. As a result, the normal incubation period which is required with the traditional Lowry method is not necessary in the practice of the method of the present invention. The Step 1 reactants may be mixed together and then immediately the Folin reagent may be added to enable the Step 2 reaction to proceed. The amount of alkali to be used has been defined above in terms of the concentration of alkali in the copper-containing solution. Although, in Step 1 of the method, the copper-containing solution is diluted by mixing with the protein-containing solution, in practice this does not result in a significant dilution of the alkali since the volume of protein-containing solution is normally no more than about one-fifth, and often considerably less, than that of the copper-containing solution. Preferably, the concentration of alkali in the copper-containing solution is from 0.2 to 2N, more preferably from 0.4 to 1N.

Although it is not preferred to use a buffering system in the present method, it is possible to moderately buffer, for instance, the alkaline copper solution and still receive most the beneficial results of the practice of this invention.

It should be appreciated that the use of a relatively large amount of alkali in Step 1 of the method of the present invention means that a correspondingly high relative amount of Folin reagent is used in Step 2. This ensures that most of the cuprous ions released as a result of the reaction between the copper (cupric) containing solution and the protein is immediately complexed or otherwise reacted with the Folin reagent. It is believed that initially a colourless product is produced which rearranges to form the coloured species.

Sodium dodecyl sulphate (SOS) may be used in the method of the present invention in order to counter the influence of nonionic and cationic detergents on the assay. For instance, the protein solution may be treated with SDS prior to the addition of Folin. Folin is preferably introduced into the copper-treated protein solution forcibly and in a volume larger than the volume of copper-treated protein. Such forced introduction of the Folin ensures that thorough mixing is achieved almost instantaneously.

It has been mentioned above that, in the second step of the method, the pH may be allowed to decrease from its initial, high, value. This is preferably accomplished rapidly. Preferably, the drop in pH is from 0.2 to 0.6 pH units in the first 10 minutes of the Step 2 reaction.

If a buffering system is used, then it is preferably present in the alkaline copper solution. A preferred buffering agent is sodium carbonate.

In one embodiment of a kit in accordance with the present invention, a buffered alkaline solution is preferably provided separately from the copper solution, the alkaline solution including sodium carbonate in a concentrated solution of alkali. In addition, a tartrate, for instance sodium or potassium tartrate, may be included in the alkaline solution. The kit is preferably provided with instructions for performing the protein assay. The reagents are preferably provided in containers of polymerised hydrocarbon in polypropylene container. The Folin is preferably supplied in a diluted ready-for-use form. SDS may be present in the alkaline solution, the copper solution or supplied as a separate solution. Preferably, it is present in the copper solution.

Another embodiment of a kit in accordance with the present invention may include the following reagents:
  an unbuffered alkaline solution, preferably containing concentrated alkali and sodium or potassium tartrate;
  a solution of a cupric salt;
  a solution of Folin phenol reagent; and
  instructions for performing the protein assay.

As before, SDS may be included in the alkaline solution, the copper solution or supplied as a separate solution. Again, it is preferred to include the SDS in the copper solution.

BRIEF DESCRIPTION OF THE DRAWINGS

A more complete appreciation of the invention and many of the attendant advantages thereof will be readily attained as the same becomes better understood by reference to the following detailed description when considered in connection with the accompanying drawings, in which

FIG. 1 shows the change in optical density (O.D.) with increasing concentration of 2% Folin reagent according to Example 1. The optical density was read after 10 minutes (plot A) and after 30 minutes (plot B). The cross over point is designated as Re.

FIG. 2 shows the change in optical density (O.D.) with times as described in Example 2. The areas marked with arrows indicate % drop in optical density.

FIG. 3 shows the change in optical density (O.D.) with time as described in Example 3.2 using unbuffered alkaline copper solution. The areas marked within vertical lines indicate % drop in optical density.

FIG. 4 shows the variation in stability of optical density with reaction commencing pH, as described in Example 3.4.

FIG. 5 shows how the release of reaction color (O.D.) can be maximized, as described in Example 4, with increasing concentration of sodium hydroxide (a, b, c, d) in an alkaline copper solution.

FIG. 6 shows how the release of reaction color (O.D.) can be maximized, as described in Example 4, with increasing concentration of Folin reagent (a, b, c) in an assay method according to the invention.

FIG. 7 shows optical density (O.D.) measurements at different Cu-protein complexing time, using the method described in Example 5.

FIG. 8 shows the reproducibility of optical density (O.D.) measurement, as described in Example 6, at pH 11.75(a) and at pH 10.5(b).

FIG. 9 shows the stability of optical density (O.D.) with time as described in Example 6. The optical density was read repeatedly for 1 hour.

FIG. 10 shows the interference by the detergent Triton-X100 on stability of a protein assay (a) and the elimination of interference as described in Example 8 by introducing sodium dodecyl sulphate into the alkaline copper solution.

FIG. 11 shows the sensitivity of an assay according to the invention, as described in Example 9, for determining low concentrations of protein.

FIG. 12 shows the tolerance of such an assay, as described in Example 10, with increasing protein concentration (a, b, c, d, e).

DESCRIPTION OF THE PREFERRED EMBODIMENTS

Figure 1:
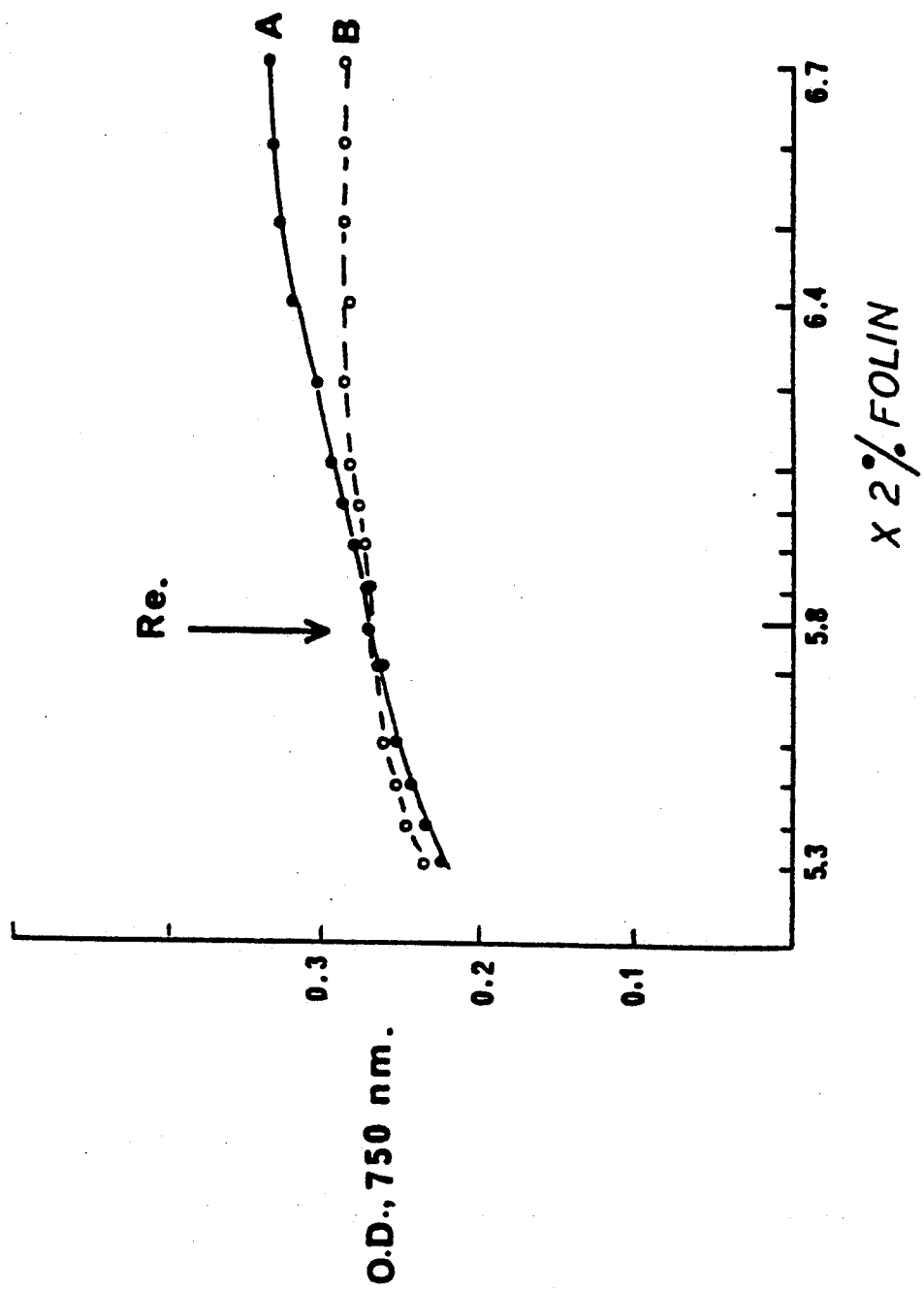
FIGS. 1 to 12 are graphs illustrating various aspects of the invention, as follows.

The protein estimation methods based on the use of Folin reagent have two constituent reagent solutions, the first of which consists of copper in solution of sodium hydroxide and sodium or potassium tartrate buffered with sodium carbonate (hereinafter referred to as buffered alkaline copper solution), and the second-of which reagent solution is Folin phenol reagent. These reagent solutions have been reported to have short shelf lives and therefore must be made fresh and prior to use.

The preparation of buffered alkaline copper solution involves making two separate solutions and mixing them just prior to use. They are:

Reagent-A, containing 2% sodium carbonate in 0.1N sodium hydroxide; and

Reagent-B, containing 0.5% copper sulphate pentahydrate in 1% sodium or potassium tartrate.

Reagent-A should be made fresh, since the solution tends to develop precipitate and solid residue in storage. Reagent-B should be made fresh by mixing equal volumes of 1% copper sulphate and 2% sodium or potassium tartrate solutions. The working buffered alkaline copper solution is recommended to be made by mixing 50 parts of Reagent-A and 1 part of Reagent-B.

The Folin phenol reagent is recommended to be made fresh from 2N concentrated Folin solution, and any unused solution should be discarded.

It has now been discovered that the dilute Folin phenol reagent can be stored for months at room temperature. It is important for long-term storage that pure de-ionised water is used in the preparation of a dilute solution of Folin reagent solution and that diluted Folin solution is protected from light. The diluted Folin solution should be stored in a container made of polymerised hydrocarbons, such as polypropylene.

It has also been discovered that a long-term storable alkaline copper solution can be prepared by keeping the constituent copper separate from the alkaline part of the reagent, and storing the alkaline solution (containing either or both sodid carbonate and sodium or potassium tartrate) in a container made of polymerised hydrocarbons, preferably in polypropylene containers. The constituent copper part can be prepared as a separate solution or with SDS, preferably in concentrated form. An appropriate portion of the concentrated copper solution is added to the alkaline solution just prior to use in order to prepare a working alkaline copper solution. It has also been discovered that such working alkaline copper solution is good for use for several weeks.

For estimation of protein in a sample, the protein is first treated with alkaline copper solution. It is widely believed that copper in alkaline medium reacts with protein and forms a copper-protein complex which in turn releases cuprous ions. It is also widely understood that the Cu-protein complex formation is a slow progressing reaction and requires several minutes of incubation for the completion of the Cu-protein reaction.

The traditional protein estimation methods based on the reaction of alkaline copper with protein invariably require incubation periods of 5 to 20 minutes in order to achieve the completion of the reaction of copper with protein.

It has been discovered that when protein is treated with alkaline copper solution containing concentrated solutions of alkali, the reaction of copper is almost instantaneous and requires no incubation for the subsequent reaction steps. In the experiments in which protein was treated with alkaline copper solution containing 0.4N and 1N sodium hydroxide, the reaction of alkaline copper with protein was almost instantaneous and required no incubation. Example 5 below clearly proves that the reaction of copper with protein was so rapid that in 15 seconds (the time it takes to vortex the mixture to achieve a uniform mixing of the reagents with protein), the reaction of alkaline copper with protein was complete, and the colour yield of the reaction was identical to the control test sample which was incubated for 20 minutes in alkaline copper. This discovery eliminates the need to incubate alkaline copper with protein which, until now, was regarded as essential. This discovery also effectively reduces the time it takes to perform protein estimation.

Folin reagent is introduced into copper-treated protein solution which results in characteristic blue colour. The methods using Folin reagent for the estimation of protein recommend the addition of an amount of Folin reagent into the copper-treated protein which would give the reaction of approximately pH 10. The addition of Folin reagent is followed by at least a 30 minutes incubation period. The reaction at pH 10 was recommended to give the maximum yield of reaction colour and a greater stability to reaction colour.

The protein assay reaction between pH 10 and 11 has several disadvantages:

at pH 10, the reaction progresses slowly and takes a long period of incubation to reach its maximum value;

30 minutes' incubation does not bring the reaction to its end-point; and the optical density of the reaction colour continues to increase for a long time after 30 minutes' incubation at a rate of 5% to 25% per hour, depending on the starting pH of the reaction mixture. The increase in optical intensity contributes to error in the protein estimation. A need exists to develop a protein assay method which would require a shorter incubation period and a stable optical density for the reaction colour, and which also gives a highly reproducible estimation of protein. Attempts have been made to reduce the incubation period after the addition a Folin reagent. Many workers have tried to heat the reaction mixture to 50° C. prior to the addition of the Folin reagent. Heating reduces the incubation period to 10 minutes. This method has serious disadvantages:

it introduces an additional step which itself takes time to accomplish; and heating tends to enhance the interference from reducing sugars and other substances (Bonitati, J., Elliot, W. B. and Miles, P. G., Alan. Biochem. 1969, 31, 399–404).

Figure 3:
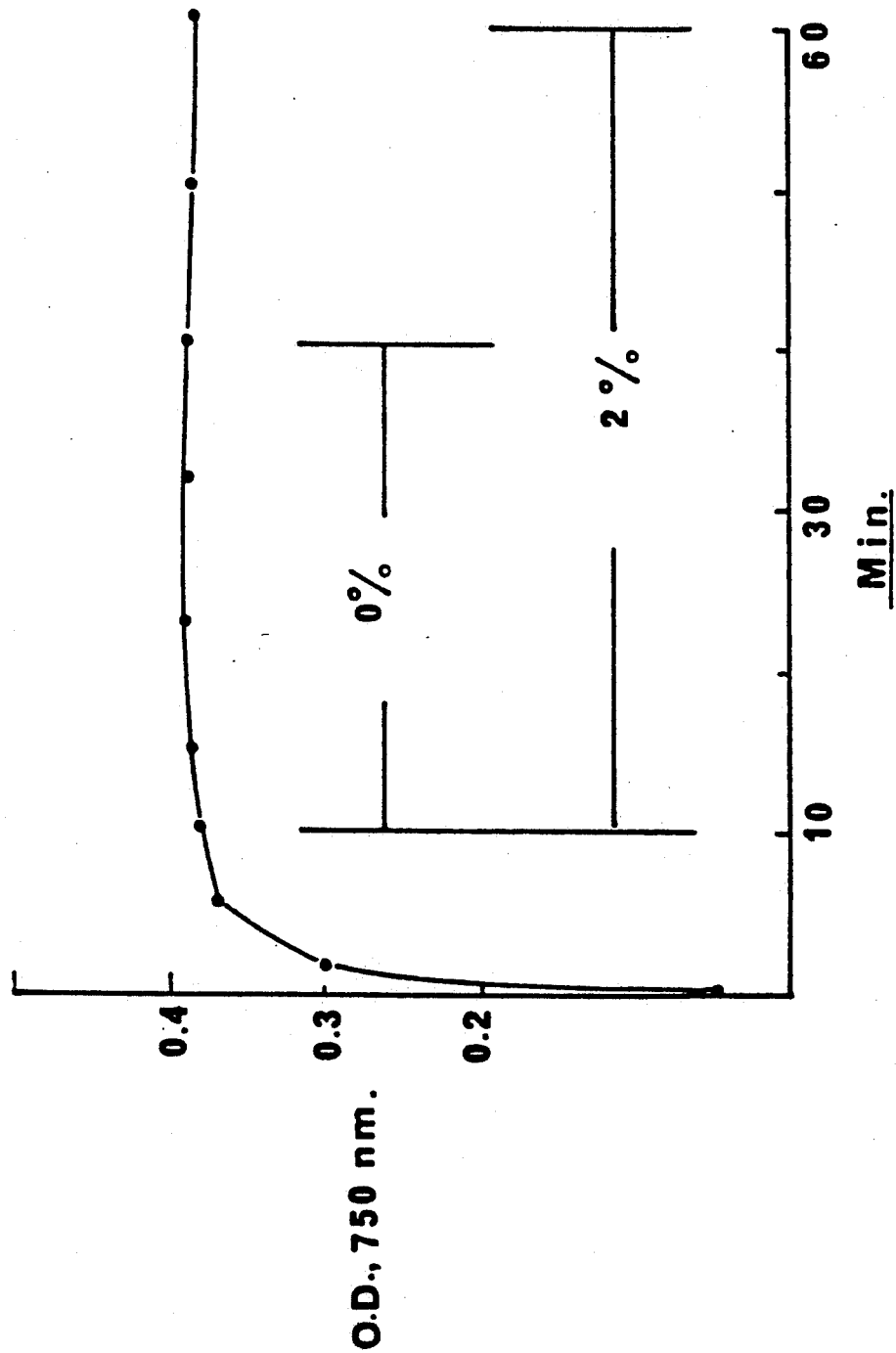
Figure 7:
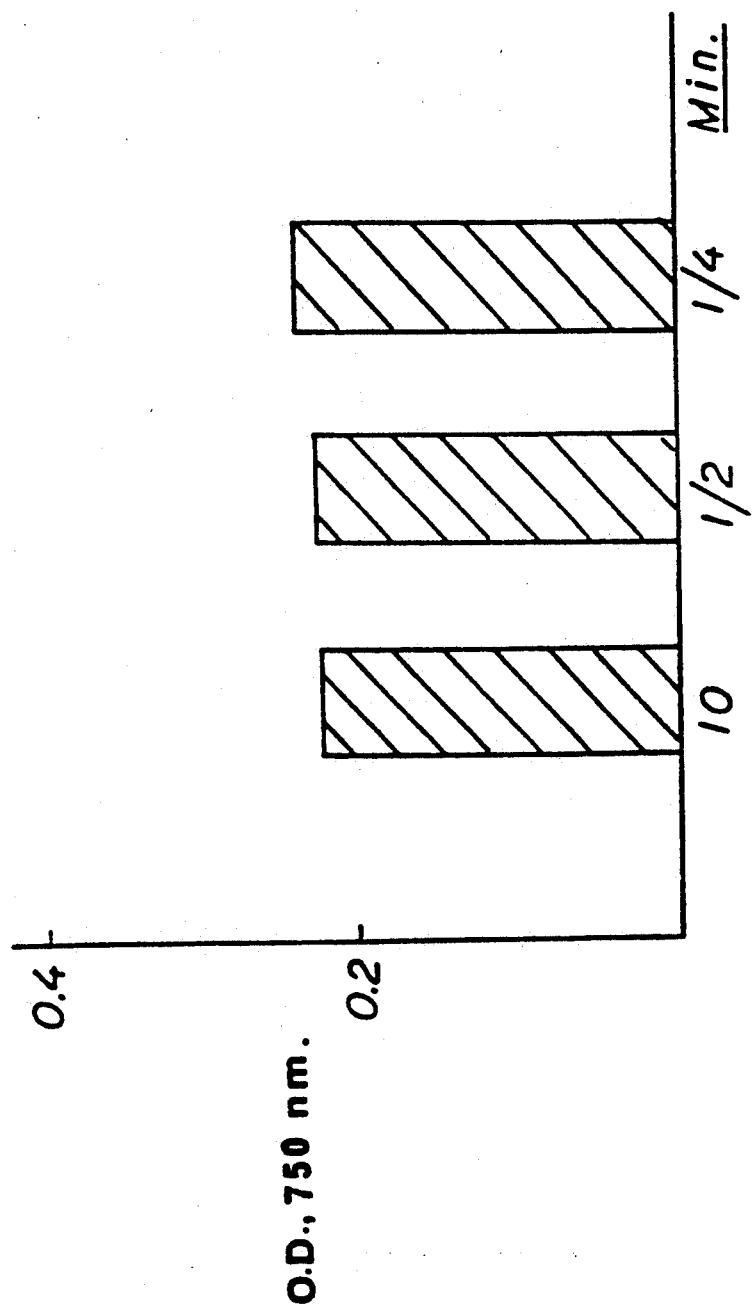
Figure 8:
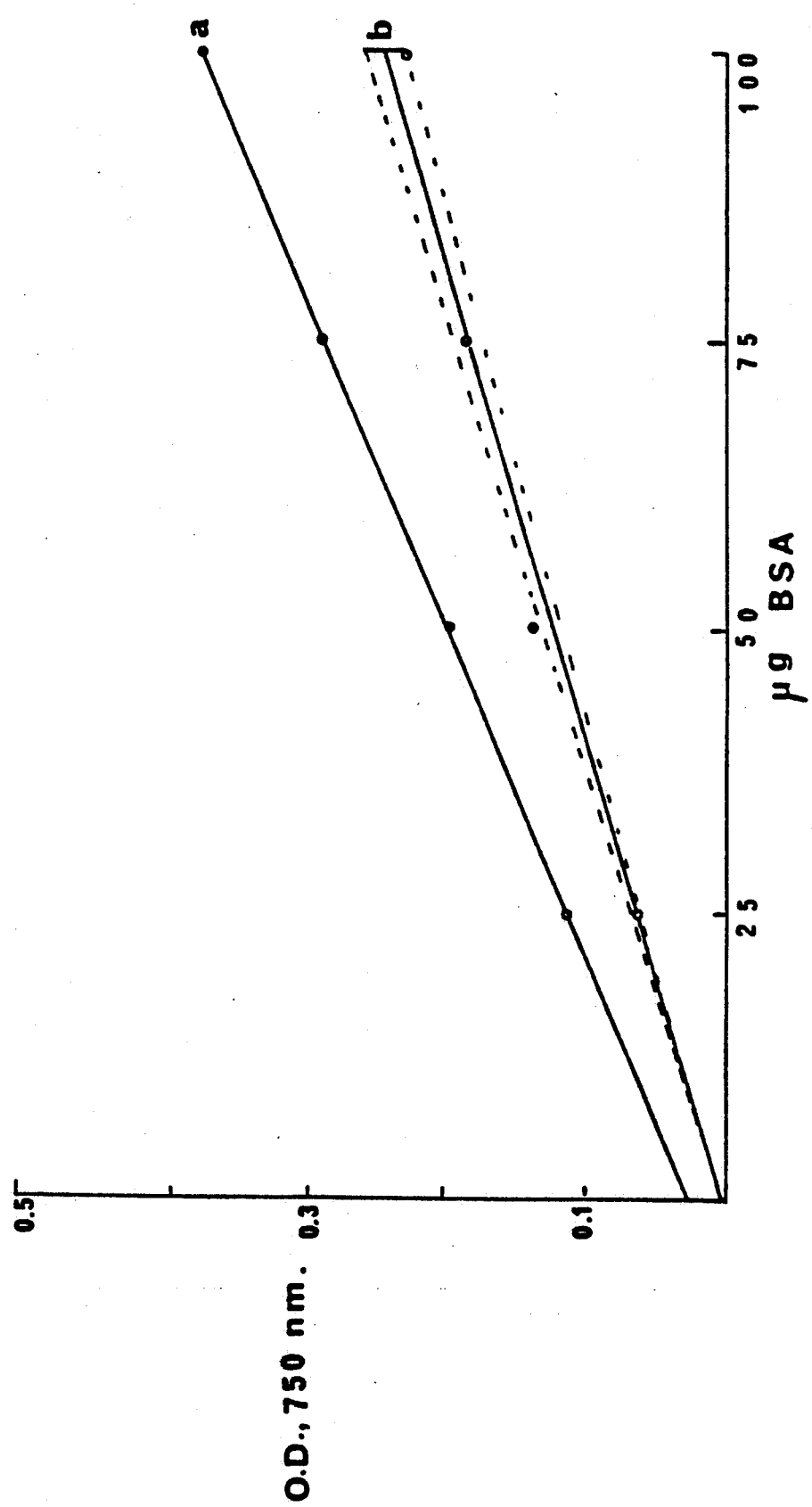

It has now been discovered that protein estimation can be performed more rapidly and with substantially increased sensitivity and reproducibility at high alkaline pH between pH 11 and 12. It has also been found that the rapid release of reaction colour between pH 11 and 12 produces results which are more reproducible than slow release as shown in FIG. 7. At pH 11–12 the reduction and colour development of Folin reagent with copper-treated protein reaches a maximum and an end-point more rapidly and, in addition, the reaction produces a plateau of stable optical density for the reaction. The higher the pH, the more rapidly colour development takes place. It has also been found that at the preferred pH of between 11.5 and 11.9, the colour development reaches a maximum and an end-point within 10 to 15 minutes, and stays nearly constant. This enables reliable determination of a large number of samples in a batch. It has also been found that after reaching the maximum, the decrease in optical density in one hour could be as little as 1% to 2% when measured in steady state, as shown in FIG. 3. However, in a real determination using duplicate samples, the draft in optical density is negligible and masked within the standard deviation of the determination, as is demonstrated in Example 6 and FIG. 8.

It has also been found possible to perform protein assay within a preselected time by preselecting the reaction commencing pH of the assay mixture and reading the reaction colour at the plateau of the maximum optical density. The preselection of assay time is made possible by carefully selecting the amounts of alkaline copper solution and Folin solution which, on mixing, could result in a pH at which the reaction colour will reach the maximum and end-point within the preselected time. Tables 1, 2 and 3 in Example 3 give the reaction commencing pH required for various preselected times, and the length of time the optical density remains nearly constant.

It has been discovered that at the reaction commencing pH in buffered alkaline medium around pH 11.70, the reduction of Folin and colour development reaches maximum in and around 10 minutes, and stays nearly constant for 15 to 20 minutes, which is sufficient to allow reading of 40-50 separate samples and in 40 minutes after reaching the end-point, maximum, the colour drift is within 3% to 4%. The optical density drift of 3% to 4% is comparable to the drift in the optical density reported for the widely used method of protein determination by Bradford M. M. (Anal. Biochem. 1976, 72, 248-254), and considerably better than the 16% drift in the optical density of another widely used method by Smith, P. K. et al (Anal. Biochem., 1985, 150, 76-85). In addition, it has also been found that, in a real determination in accordance with the present invention, the expected drift was not detected as is shown in example 3.1 and FIG. 8.

A further improvement in the reaction is achieved when unbuffered alkaline medium is used for the assay. In unbuffered alkaline medium, the pH of the reaction drops unhindered and more rapidly, and in less than 10 minutes the pH drops as much as 0.15-0.6 units for a reaction commencing between pH 11 and 12 (Table 2, FIG. 3). This finding has two advantages:

it allows a rapid release of reaction colour at a very high alkaline pH; and as soon as the maximum reaction colour is achieved and before substantial decomposition of colour could begin, the pH of the reaction also shifts to a pH at which the decomposition of the reaction colour is very considerably reduced (Tables 1 and 2, FIG. 3).

The reaction shown in FIG. 3 commences at a pH around 11.70. In less than 10 minutes the release of colour reaches a maximum value and concurrently the pH of the reaction drops by 0.2 units to pH 11.5. At pH 11.5, the optical density of reaction colour is virtually unchanged for over 30 minutes (Tables 1 and 2, FIG. 3) and in the next 30 minutes, the optical density drops by a mere 2% to 3%. The shift in optical density of 2% to 3% in the second half hour of a one-hour period is less than the method of Bradford cited above.

Previous workers have tried to buffer the drop of pH brought about by the reduction of Folin. It is quite clear from the studies carried out in this invention that the drop in the pH has positively beneficial effects, first in bringing down the time it takes the reaction to reach a maximum value and, secondly, the drop of the reaction pH to a lower pH improves the stability of the reaction colour.

In a further study, neither sodium carbonate nor sodium tartrate were present in the alkaline copper solution. The removal of tartrate from the alkaline copper solution lowered the rate of reduction of Folin with copper-treated protein and consequently it took longer for the reaction colour to reach a maximum value, and at maximum the reaction colour is generally more stable. The results in Table 3 show that the reaction commencing at pH 12 took approximately 10-12 minutes to reach the maximum as compared to 5 minutes in unbuffered and buffered alkaline solution (Tables 1 and 2). In addition, in the absence of tartrate, the reaction colour is more stable after reaching the maximum value as shown in Table 3.

When Folin is added to the copper-treated protein, maximum colour results if the reduction occurs at a pH around pH 10. The reduction of Folin at higher pH between pH 11-12 results in lowering of the yield of reaction colour and consequently reduces the sensitivity of the method. It has been discovered that the colour yield of the reaction at higher alkaline pH could be increased to its maximum value or to a level which is comparable to the traditional methods based on the use of Folin reagent. The yield of reaction colour is maximised by increasing the amount of Folin in the assay, which is achieved by increasing the concentration of alkali in the alkaline copper solution. Example 5 shows that as the concentration of alkali is increased in the alkaline copper, it requires correspondingly increased amounts of Folin to achieve a pH of around 11.7 and consequently the colour yield is increased to a much higher value than would be possible to achieve at pH 10 in 10-15 minutes. Example 7 demonstrates increased sensitivity of the method of the invention over the Lowry method.

It has also been discovered that rapid release of reaction colour at a relatively higher alkaline pH, i.e. pH 11-12, results in improved reproducibility of protein estimation. Plot A of Example 6 shows a typical estimation of protein using the method described in this invention. The points in the plot make a perfect straight line, leaving no room for ambiguity. Plot B on the other hand is based on the determination at pH 10.5, the points on the plot are scattered and it is possible to draw more than one straight line through the points.

When Folin is added to the protein treated with alkaline copper, the reagent is only reactive for a short time, and it is for this reason that Folin is preferably added while vortexing the reaction mixture. It is difficult to achieve uniformity with a large number of samples in a batch while adding Folin to a vortexing mixture. It has been found that this problem can be eliminated by keeping the volume of copper-treated protein small and introducing Folin forcibly in a volume larger than the volume of copper-treated protein. The forcible addition of Folin creates instantaneous mixing of Folin with copper-treated protein which ensures uniform mixing of the reagents in a batch.

The protein assay methods based on reduction of Folin by copper-treated protein suffer from interference by a number of commonly used laboratory reagents, and particularly nonionic and cationic detergents, such as Triton-X100. This interference from nonionic and cationic detergents can be eliminated by introducing in the assay, prior to the addition of Folin, a small amount of anionic detergent such as SDS. This could be achieved by the addition of SDS in the alkaline copper solution. Example 8 shows that addition of SDS eliminates interference by Triton-X100.

It has also been found that it is difficult to maintain SDS in a solution of sodium hydroxide having a concentration higher than 0.4N. SDS in as low a concentration of 0.5% has a tendency to precipitate on standing in sodium hydroxide solution higher than 0.4N. It is recommended that SDS is kept separate from the alkaline part and mixed prior to use. The solution may be warmed to maintain the SDS in solution.

SDS can be dissolved either with tartrate or copper sulphate and stored for a long time. SDS solution containing copper sulphate can be mixed with alkaline solution in order to prepare the alkaline copper solution.

The materials and preparation used in the following Examples are as follows:

Reagents

Copper sulphate pentahydrate, potassium tartrate, sodium tartrate, sodium carbonate, sodium hydroxide, sodium dodecyl sulphate (SDS) and bovine serum albumin (BSA) were obtained from Sigma Chemical Co. Alkaline copper solution was made in two parts, the first part (hereinafter referred to as "the alkaline solution") of which contained sodium hydroxide, sodium carbonate sodium or potassium tartrate and SDS, which were added to the alkaline solution only when specified. The second part was a concentrated solution of copper sulphate. The Folin reagent solution was made using a 2N Folin reagent solution.

Reagent Preparation

Various concentrations of alkaline solution were prepared. They were 0.4N, 0.8N, 1N and 2N sodium hydroxide solution. Either 4% or 5% sodium carbonate and 0.16% sodium tartrate were added to the alkaline solution only when specified. Similarly, SDS was added to the alkaline solution only when specified to a final concentration of 0.5% to 2%. The alkaline solution was stored at room temperature in polypropylene bottles. A 5% copper sulphate solution was made in distilled water and stored at room temperature in a polypropylene bottle. The working alkaline copper solution was made by mixing 10 ml of alkaline solution with 0.1 ml of 5% copper sulphate solution.

Folin solutions were made using Pure de-ionised water. 2%, 5% and 10% Folin solutions were made using a 2N Folin solution and stored at room temperature in polypropylene bottles protected from light. Bovine serum albumin (BSA) was dissolved in distilled water to a final concentration of 2 mg/ml and used as standard stock.

Protein Assay Method

Protein solution containing 10 to 200 μg protein in a volume 0.05 to 0.2 ml were pipetted into test tubes. The alkaline copper solution was added to the test tubes in a volume equal to 1-5 times the volume of protein solution in the test tubes, and vortexed. Immediately after vortexing, unless otherwise specified, an appropriate volume of Folin reagent solution was forcibly introduced into the test tubes. The test tubes were incubated for 10 minutes at room temperature and absorbency at 650-750 nm was measured. The weight of protein was plotted against the corresponding absorbence resulting in a standard curve used to determine the protein in unknown samples.

Micro Protein Assay

Protein solutions containing 1 to 8 μg protein in a volume of 5 μl were pipetted into either micro test tubes or microtiter plates. Alkaline copper solution was added into the micro test tubes in a volume equal to 4-5 times the volume of protein solution, i.e. 20-25 μl. An appropriate volume of Folin reagent solution was forcibly introduced in the micro test tubes. The micro test tubes or microtiter plates were incubated at room temperature for 10 minutes and then absorbences at 650-750 nm were read. The weight of protein was plotted against the corresponding absorbence, resulting in a standard curve used to determine the protein in unknown samples.

EXAMPLE 1

Determination of Short Incubation Period in Assay

A series of duplicate samples of standard protein solution containing 0.2 mg protein in a volume of 0.1 ml were treated with 0.5 ml of alkaline copper solution containing 0.4N NaOH in 4% sodium carbonate, 0.16% sodium tartrate and 0.05% copper sulphate. After mixing, the contents were treated with increasing volume of 2% Folin reagent introduced forcibly. The volume of 2% Folin was increased from 5.2 times the total volume of copper-treated protein (i.e. 0.6 ml) to 6.7 times. The optical density was read after 10 minutes (Plot B) and after 30 minutes (plot A) incubations at room temperature. The results gave the plots shown in FIG. 1. As seen from the graph, the optical density taken after 30 minutes' incubation (Plot A) crosses over the optical density taken after 10 minutes' incubation (Plot B). The crossover point is referred to in the graph as "Re" and marked with an arrow. The crossover point has a reaction commencing pH of around pH 11.70. It is clear from the graph that the reduction of Folin with copper-treated protein at pH around pH 11.7 reached its end-point maximum in around 10 minutes, and the optical density remained unchanged for the next 20 minutes. The reduction of Folin at a pH significantly higher than pH 11.70 begins to decline rapidly after 10 minutes and, similarly, the reduction of Folin at pH significantly lower than pH 11.70 continues to increase after 10 minutes' incubation. It is clear from these graphs that a protein assay method based on the reduction of Folin at a pH around pH 11.70 can be developed which will reduce the incubation period to around 10 minutes. At a pH of around 11.70 the optical density stays nearly constant for long enough to allow assay of a large number of samples without significant drift in determination.

EXAMPLE 2

Determination of Stability of Reaction Colour

Figure 2:
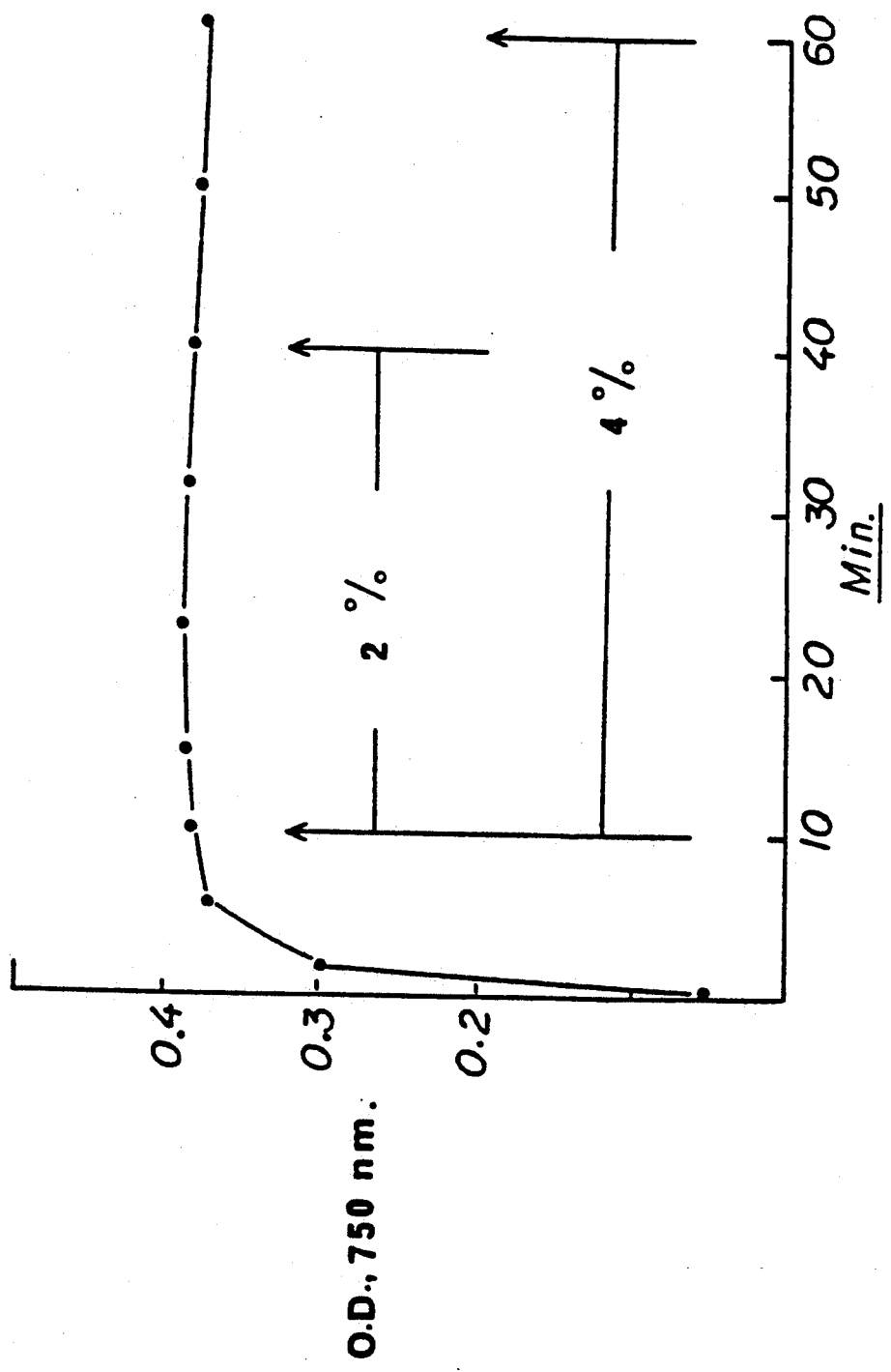

A sample of standard protein solution containing 0.1 mg protein in 0.1 ml was mixed with 0.5 ml of alkaline copper solution containing 1N NaOH in 5% sodium carbonate, 0.164 sodium tartrate and 0.05% copper sulphate. After mixing, 3.55 ml of 5% Folin reagent was forcibly introduced. A 1 ml portion was removed for pH determination, and the remainder was used to measure the optical density. The optical density was continuously measured for one hour. The pH at the commencement of the reaction was measured within 1.5 minutes, which was approximately pH 11.70. the optical density result gave the plot shown in FIG. 2. It is clear from the graph that the reduction of Folin commencing at a pH around pH 11.70 caused rapidly increased optical density and reached its end-point maximum in around 10 minutes, which changed very little for the next 50 minutes. It was estimated that, after reaching the end-point maximum in 10 minutes and for the next 15-20 minutes, the decline in optical density was negligible (around 1%) and in the subsequent 20-25 minutes, it was around 3%-4%. An overall drift in the optical density of 3%-4% in one hour is comparable to the widely used method by Bradford, M. M. (Anal. Biochem. 1976, 72, 248-254) and considerably better than the 16% drift in the optical density of another popular method by Smith, P. K. (Anal. Biochem., 1985, 150, 76–85). The results also show that in a 45-minute period, the pH of the reaction gradually drops by approximately 0.2 units.

In a similar experiment to that described above, the protein was treated with unbuffered alkaline copper solution containing 0.16% sodium tartrate and 0.5% copper sulphate in 1N NaOH. After mixing, 3.7 ml of 5% Folin reagent was forcibly introduced and the reaction pH was read within 1.5 minutes of mixing: this was around pH 11.70. The optical density gave the plot shown in FIG. 3. The result shows rapid reduction of Folin, which reaches a maximum within 10 minutes. The optical density remained virtually unchanged for over 30 minutes and, after that, it began to decline gradually. In a 60-minute period, the drift in reaction colour is around 2%–3%, which is a considerable improvement on the example described above. The result also shows that the pH drops by approximately 0.2 units in the first 10 minutes, and approximately 0.3 units in 30 minutes, of the reaction.

EXAMPLE 3.1

Stability of Optical Density at Various Reaction pH in Buffered Medium

A sample of standard protein solution containing 0.1 mg protein in 0.1 ml was mixed with 0.5 ml of buffered alkaline copper solution containing 1N NaOH in 5% sodium carbonate, 0.16% sodium tartrate and 0.05% copper sulphate. The copper-treated protein solution was treated with increasing amounts of 5% Folin (3.1 ml to 4.6 ml). The optical density of reaction colour was recorded and the pH of the reaction was recorded at intervals. The results were tabulated as shown in Table 1.

TABLE 1

| Volume of 5% Folin (ml) | Approximate Reaction pH 0    45 (Minutes) | Approximate Time to Reach Maximum (Minutes) | Approximate Length of Plateau at Maximum (Minutes) |
|---|---|---|---|
| 3.1 | 12.10–11.95 | 4–5 | 4–5 |
| 3.2 | 12.00–11.88 | 5–6 | 6–8 |
| 3.3 | 11.95–11.75 | 6–7 | 8–9 |
| 3.4 | 11.85–11.62 | 6–8 | 10–12 |
| 3.5 | 11.75–11.58 | 8–10 | 20–22 |
| 3.6 | 11.65–11.40 | 10–12 | 25–30 |
| 3.7 | 11.55–11.30 | 13–14 | 40–45 |
| 3.8 | 11.53–11.30 | 15–17 | >50 |
| 3.9 | 11.40–11.12 | 16–18 | >60 |
| 4.1 | 11.23–11.95 | 18–20 | >60 |
| 4.3 | 11.10– | 32–34 | >60 |

It is clear from the Table above that the reduction of Folin with copper-treated protein commencing at a pH of between 11.8 and 11.60 reached its end-point maximum in around 8–10 minutes. After reaching its maximum, and for the next 15–20 minutes, the optical density remains nearly constant. The deviation in optical density in a 30-minute period was negligible at around 1%. The deviation in the subsequent 30 minutes was around 3%–4% (not shown in Table 1). The reduction of Folin commencing at a ph of between 11.60 and 11.40 reached its maximum in around 15–20 minutes and stayed nearly constant for 30–40 minutes. In the subsequent 30 minutes, the decline in optical density was around 3% to 4%.

It is clear from Table 1 that the higher the alkalinity of the reaction, the more rapidly production of reaction colour takes place and, conversely, the higher the alkalinity, the shorter is the length of the plateau at the maximum optical density. At the reaction pH 11.75, a reasonable balance is struck and the reaction takes under 10 minutes to reach its maximum colour, while the plateau at the maximum lasts around 15–20 minutes. The reaction commencing at pH 11.50 would take around 20 minutes to reach the maximum colour, and the colour at the maximum would remain unchanged for over 30 minutes. Lowering the alkalinity substantially increases the time it takes to reach the maximum reaction colour, although it also increases the stability of the reaction colour. It has also been found that the rate of decomposition or the reaction colour is considerably reduced by lowering the alkalinity (not shown in this table). The reaction colour is stable for over 30 minutes when the pH at the plateau is lowered to around pH 11.50 and beyond. It is also clear from Table 1 that, in buffered alkaline medium, during the course of reaction the pH of the reaction mixture gradually decreases, and in 45 minutes the pH decreases by approximately 0.2 units.

EXAMPLE 3.2

Stability of Optical Density at Various Reaction pH in Unbuffered Medium

A sample of standard protein solution containing 0.1 mg protein in 0.1 ml was mixed with 0.5 ml of unbuffered alkaline solution of copper, containing 1N NaOH in 0.16% sodium tartrate and 0.05% copper sulphate. The copper-treated protein was treated with increasing amounts of 5% Folin (3.4–4.0 ml). The optical density of the reaction colour was recorded, and the pH of the reaction was recorded at intervals. The results were recorded in Table 2 and FIG. 3.

TABLE 2

| Volume 5% Folin (ml) | Approx. Reaction pH 0    15    45 (Minutes) | Approx. Time to Reaction Maximum (Minutes) | Approx. Length of Plateau at Maximum (Minutes) |
|---|---|---|---|
| 3.4 | 11.95–11.77–11.65 | 5–6 | 10–11 |
| 3.5 | 11.87–11.70–11.58 | 8–9 | 18–20 |
| 3.6 | 11.80–11.60–11.50 | 9–10 | 24–26 |
| 3.7 | 11.75–11.58–11.48 | 9–10 | 26–28 |
| 3.75 | 11.73–11.53–11.45 | 10–11 | 28–30 |
| 3.8 | 11.65–11.49–11.33 | 16–18 | 50–55 |
| 4.0 | 11.55–11.33–11.20 | 30–35 | >75 |

It is clear from the results that in unbuffered alkaline medium, the pH of the reaction mixture drops more rapidly than in the buffered medium (Table 1), and a drop of approximately pH 0.2 units takes place in under 10 minutes. Consequently, when the reaction is commenced at around pH 11.70, it rapidly releases the reaction colour and reaches a maximum in around 10 minutes. The reaction releases acid and, as a result, the pH drops to around pH 11.50 which happens to be a pH at which the reaction is nearly unchanged for well over 30 minutes (Table 1).

The overall effect is a rapid release of reaction colour at a very high alkaline medium (in around 10 minutes) and, as the maximum reaction colour is reached, the pH of the reaction drops to a pH at which the decomposition of the colour in 60 minutes is insignificant. It has been found that in a 60-minute period the drift in optical density is around 2%.

EXAMPLE 3.3

Rate of Folin Reduction and Stability of Reaction Colour in the absence of Tartrate in Unbuffered Alkaline Copper Solution The experiments were performed as described in Example 3.2, except that tartrate was not added in the alkaline copper solution. The results, shown in Table 3, show that in the absence of tartrate the reduction of Folin by copper-treated protein proceeds slowly.

TABLE 3

| Volume 5% Folin (ml) | Approx. Reaction pH 0   15   45 (Minutes) | Approx. Time to Reaction Maximum (Minutes) | Approx. Length of Plateau at Maximum (Minutes) |
|---|---|---|---|
| 3.4 | 11.95–11.75–11.61 | 10–12 | 24–25 |
| 3.6 | 11.78–11.60–11.49 | 14–16 | 28–30 |
| 3.7 | 11.68–11.48–11.33 | 17–18 | 60–65 |
| 3.8 | 11.65–11.40–11.30 | 25–27 | >65 |

The results in Table 3 show that the reaction commencing at pH 12 took approximately 10–12 minutes to reach the maximum as compared to 5 minutes in unbuffered and buffered alkaline solution as shown in Tables 1 and 2. In addition, in the absence of tartrate, the reaction colour was more stable after reaching the maximum value.

EXAMPLE 3.4

A Model for Protein Assay at High Alkaline pH

Figure 4:
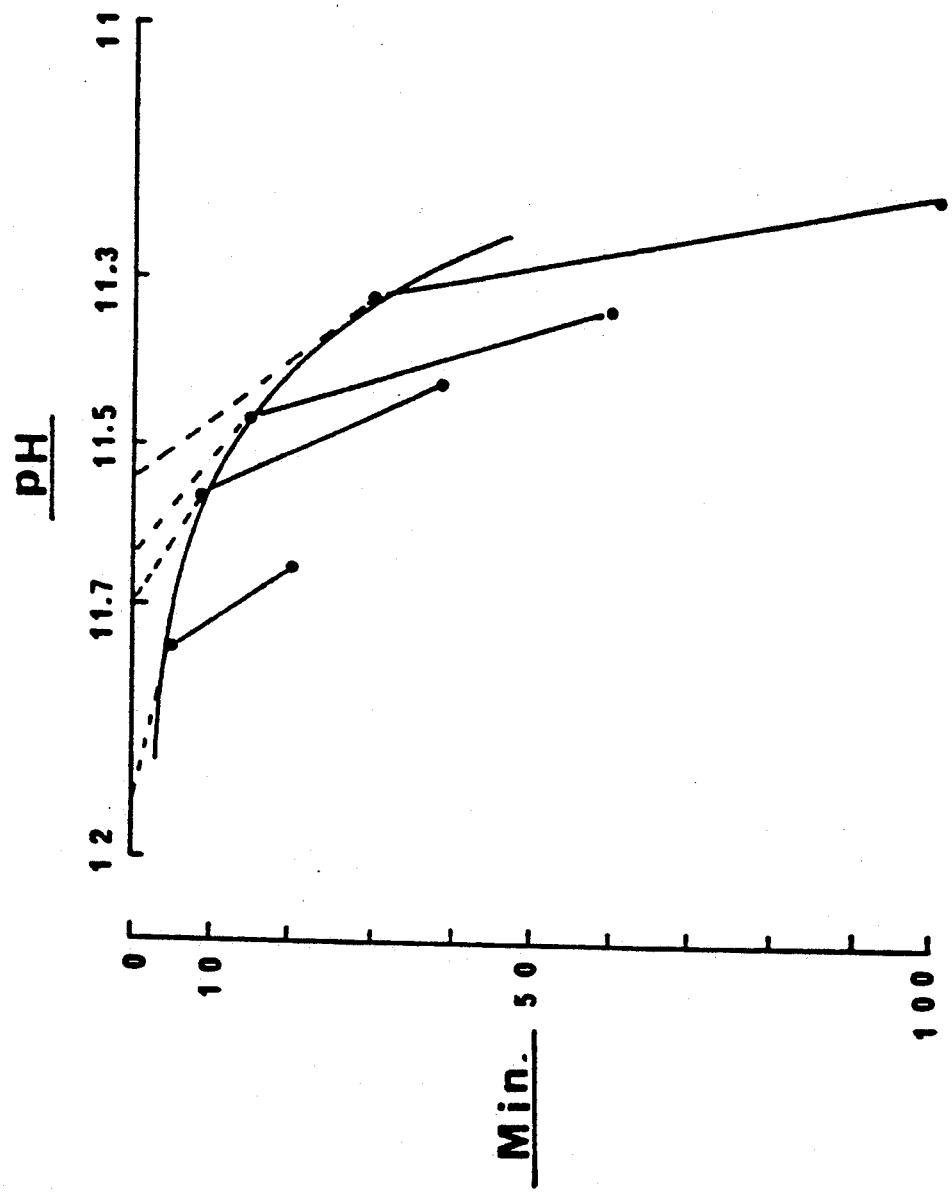

The results of Example 3.2 were plotted to create a model for protein assay at high alkaline pH. FIG. 4 shows the plot. Reaction commencing pH was plotted against time. The broken lines show the changes in the reaction pH before reaction colour optical density reached a maximum value. The semicircle represents the time, corresponding to reaction commencing pH, that it takes a reaction to reach its maximum value. The solid lines show the length of time the optical density of reaction colour remained stable. It is clear from the model that the higher the alkalinity of the reaction, the more rapidly the release of reaction colour takes place. Conversely, the higher the alkalinity, the shorter is the length of stable optical density at maximum. When reduction of Folin commences at a pH around 11.7, it reached the maximum reaction colour in approximately 10 minutes. Having reached the maximum value, the reaction colour optical density remained virtually unchanged for the next 30 minutes.

EXAMPLE 4

Maximising the Release of Reaction Colour

Figure 5:
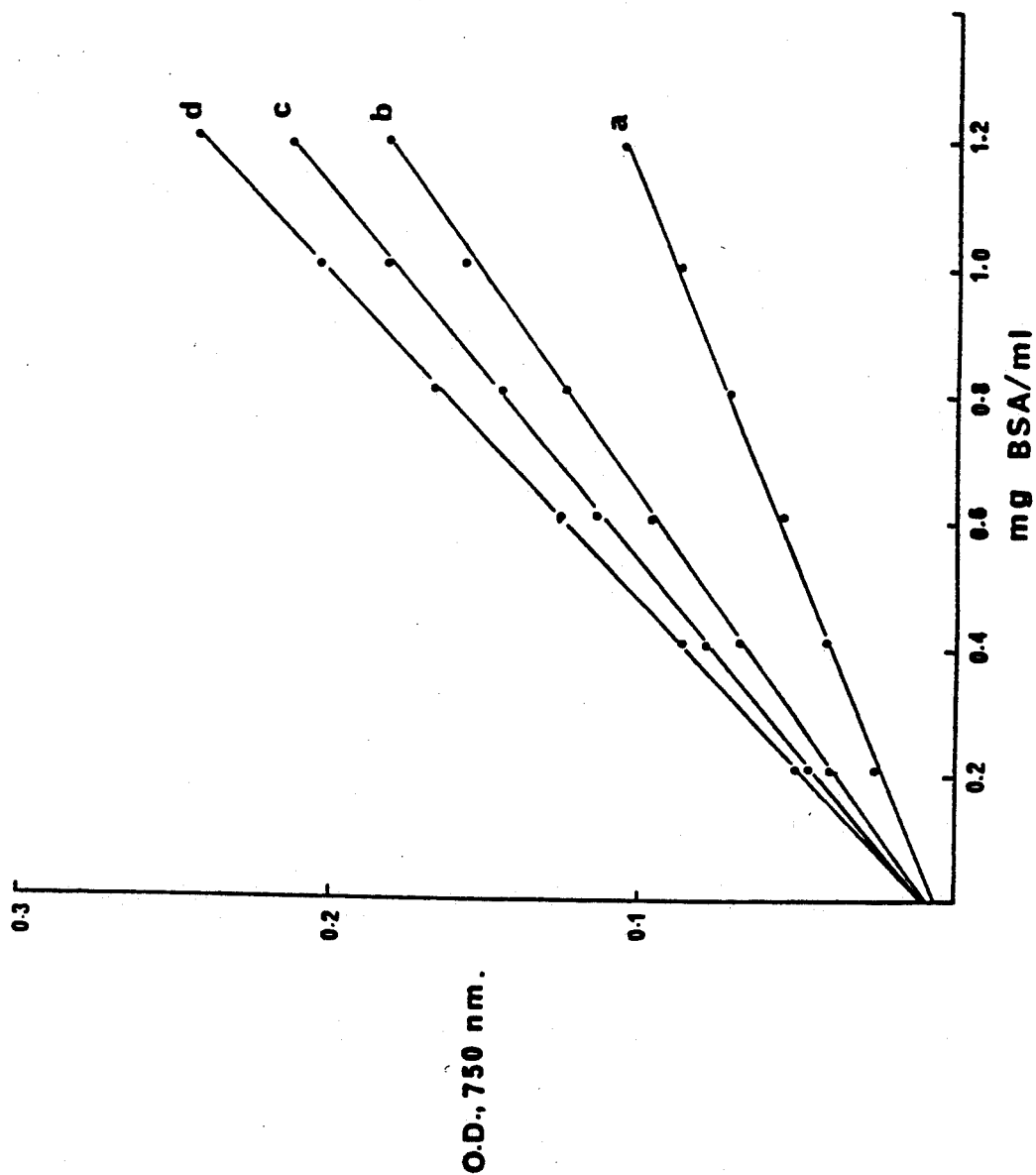

The experiment consisted of a batch of four determinations, a, b, c and d. Duplicate samples of 0.1 ml protein solution containing 0.2–1.2 mg/ml were pipetted for each batch. Batches a, b, c and d were treated with 0.1, 0.2, 0.3 and 0.4 ml alkaline copper solution (containing 0.4N NaOH in 4% sodium carbonate, 0.16% sodium tartrate and 0.05% copper sulphate respectively). After mixing the contents, 1.16, 1.74, 2.32 and 2.9 ml of 2% Folin reagent was forcibly added to a, b, c and d respectively. After an incubation of 10 minutes, the optical density was read and the results gave the plots shown in FIG. 5.

The next experiment consisted of a batch of three determinations, a, b and c. Duplicate samples of 0.1 ml protein solution containing 0.2–1.2 mg/ml were pipetted for each batch. The protein solutions were treated with 0.5 ml alkaline copper solutions, the compositions of which are as follows:

1. 0.4N NaOH containing 4% sodium carbonate, 0.16% sodium tartrate and 0.05% copper sulphate;
2. 1N NaOH containing 5% sodium carbonate, 0.16% sodium tartrate and 0.05% copper sulphate;
3. 2N NaOH containing 5% sodium carbonate, 0.16% sodium tartrate and 0.05% copper sulphate.

Figure 6:
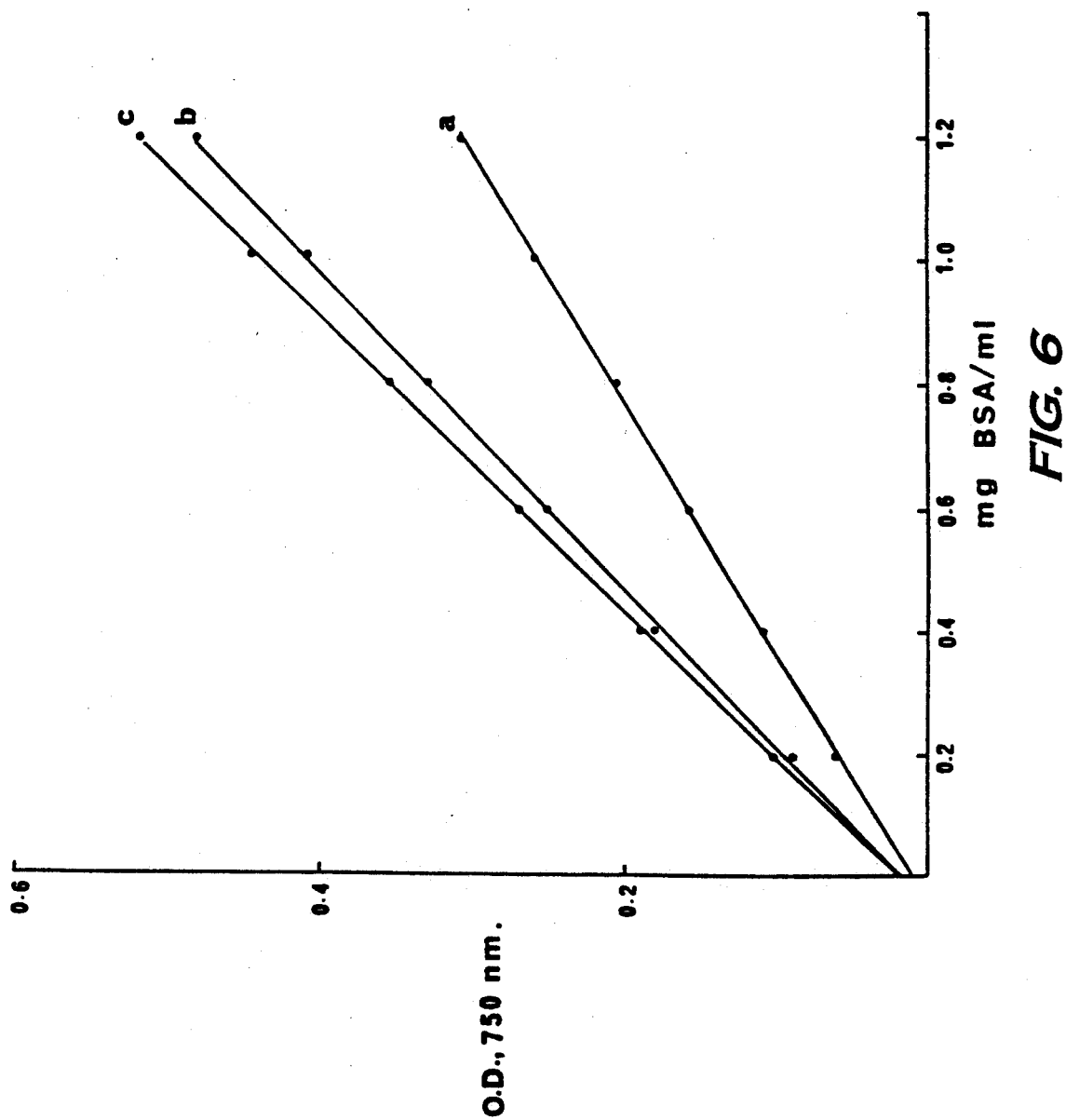

Batches a, b and c were treated with alkaline copper solution 1, 2 and 3 respectively. After mixing the contents, batches a, b and c were treated with 3.5 ml of 2%, 5% and 10% Folin reagent respectively. The optical density was recorded and the results gave the plots shown in FIG. 6. It is clear from FIGS. 5 and 6 that the release of reaction colour can be increased and mazimised by increasing either the amount or the concentration of alkali and correspondingly increasing the amount of Folin solution in the assay.

EXAMPLE 5

Determination of Cu-Protein Complexing Time

Triplicate protein solutions containing 0.1 mg of protein in 0.1 ml were mixed with 0.5 ml of alkaline copper solution containing 1N NaOH in 5% sodium carbonate, 0.16% sodium tartrate and 0.05% copper sulphate. The contents were mixed immediately and, without delay, 3.5 ml of 5% Folin solution was forcibly introduced. The whole procedure took around 15 seconds to complete. Three more samples were treated identically except that Folin solution was added after an incubation period of ½, 1 and 10 minutes. The optical density was read after 10 minutes and the results gave the histogram shown in FIG. 8. It is clear from the results that copper complexed with protein immediately after the addition and mixing. Similar results were obtained when protein was treated with alkaline copper solution containing 0.4N NaOH. It is clear that copper complexed with protein immediately in alkaline solution containing as little as 0.4N NaOH.

EXAMPLE 6

Reproducibility and Accuracy of the Assay

Reproducibility and accuracy of the assay was examined by performing identical determinations. Samples containing 0.0250–0.1 mg/ml were mixed with 0.5 ml of alkaline copper solution containing 1N NaOH in 5% sodium carbonate, 0.16% sodium tartrate and 0.05% copper sulphate. After vortexing the mixture, 3.5 ml of 5% Folin solution was forcibly introduced into the copper-treated protein solution. The pH of the reaction mixture was measured around 11.75. The optical density of the assay reached its maximum in around 10 minutes. The optical density was repeatedly read after 10 minutes, and the results gave Plot A shown in FIG. 8. An identical determination was also performed in which the reaction was commenced at pH 10.5, and the results gave Plot B shown in FIG. 7. The results show clearly that the protein estimation based on the method described in this invention produces highly reproducible results. In Plot A, the points give a perfect straight line and, on the other hand, the estimation based on pH 10.5 of the reaction has a larger deviation (Plot B).

Figure 9:
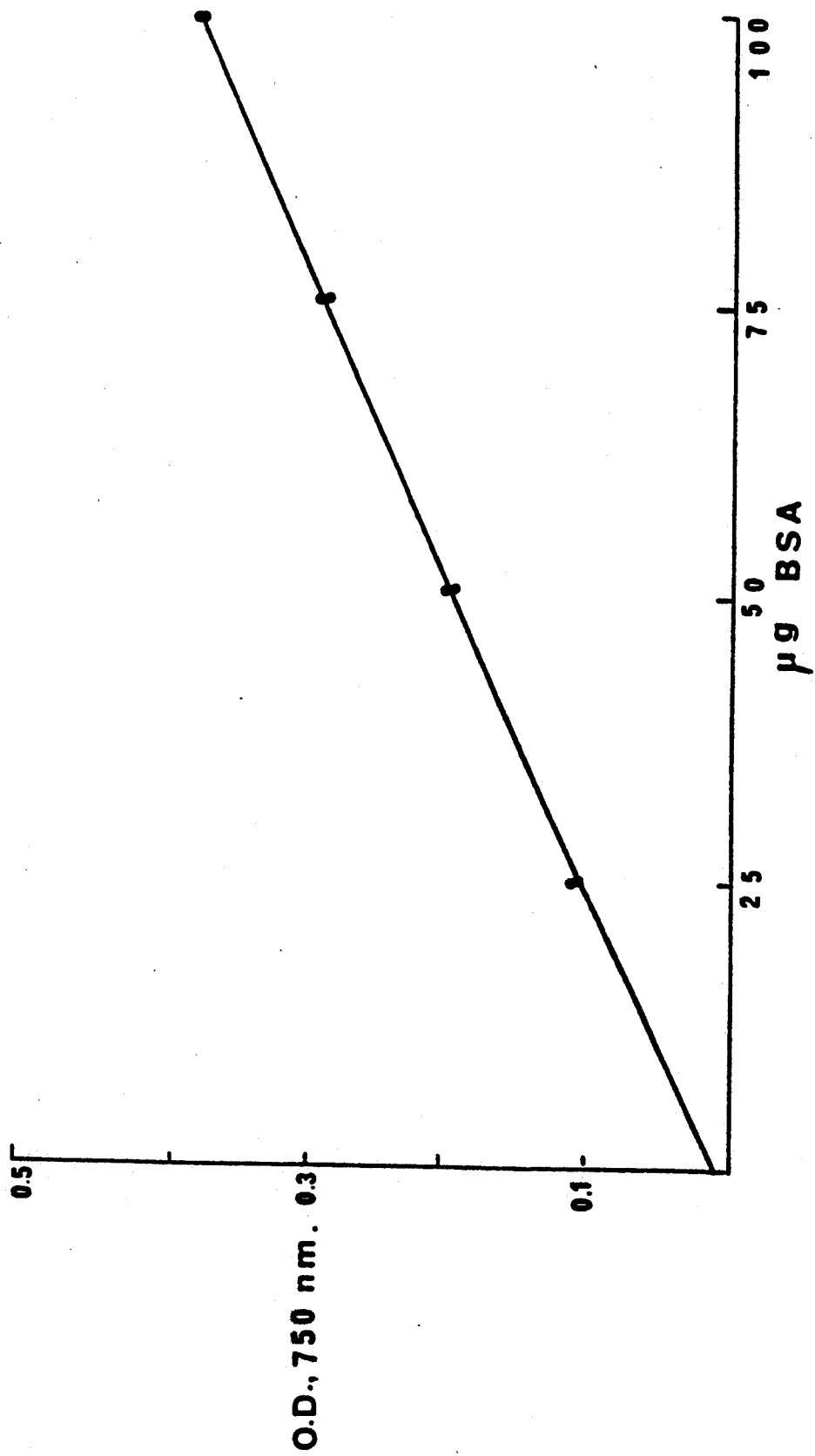

In a further extension of this experiment, the samples of Plot A were repeatedly read for an hour, and the results are shown in FIG. 9. The result shows clearly that in a one-hour measurement, the expected drift in the optical density was not detected, and the points were closely parked. The inclination of the standard plot remained unchanged. The method described in this invention is therefore highly reproducible and reliable for estimation of protein.

EXAMPLE 7

Sensitivity of the Assay

The sensitivity of the assay was assessed by comparing it with the results produced by the Lowry method. Duplicate samples of protein solution containing 0.025-0.1 mg/ml in a volume of 0.1 ml was assayed as described in Example 6 and by the Lowry method. The results gave the plots shown in FIG. 8. It is clear from the graph that the assay performed according to the method described in this invention is more sensitive than the Lowry method.

EXAMPLE 8

Elimination for Interference

Figure 10:
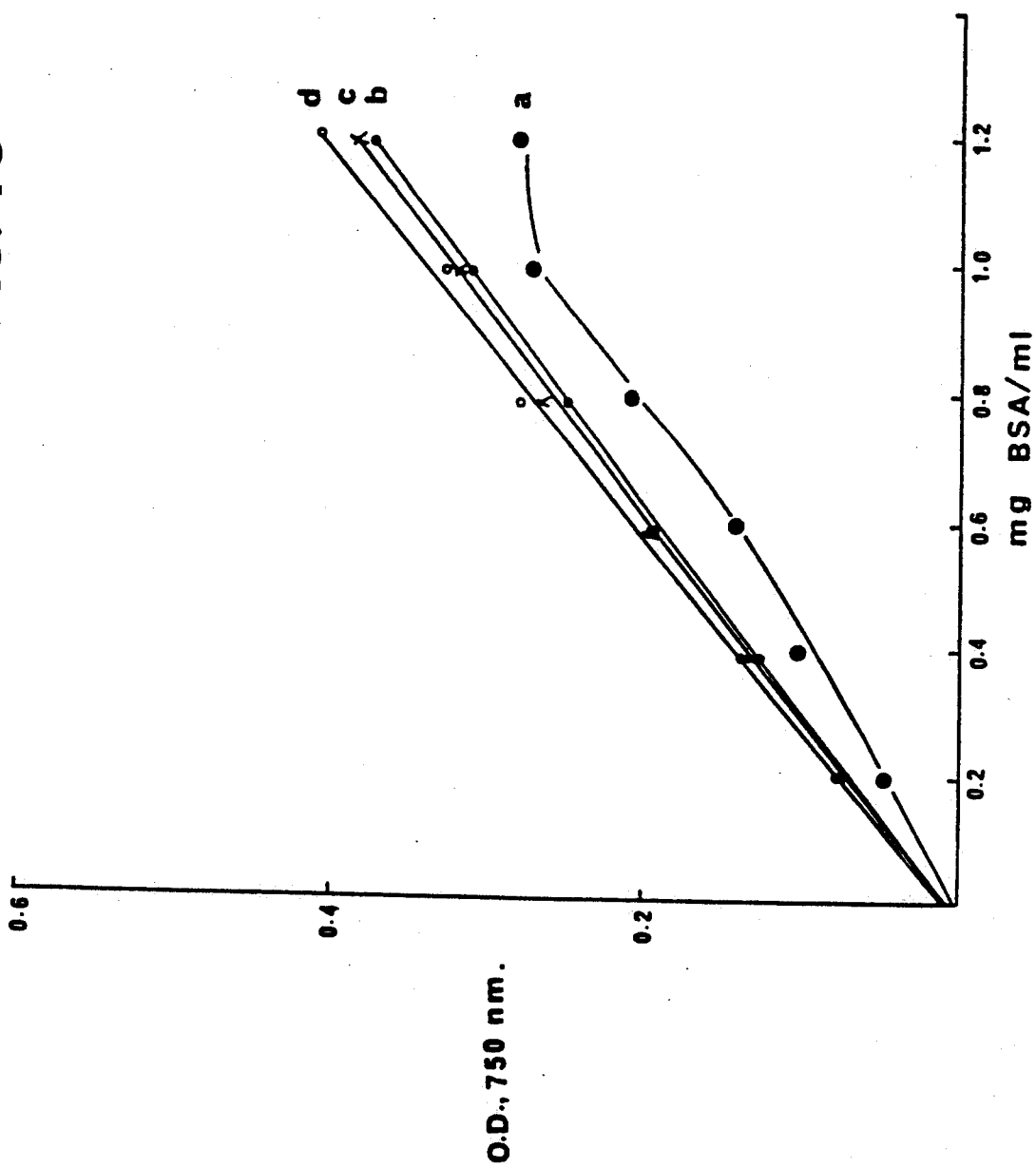

Protein assays using Folin reagent are sensitive to interference by a number of commonly used laboratory reagents. The small effects due to such agents as sucrose, EDTA, Tris and 2-mercaptoethanol can be easily eliminated by running a proper buffer control with the assay. The interference by nonionic and cationic detergents can be eliminated by introducing a small amount of anionic detergent sodium dodecyl sulphate (SDS) (0.5% -2%) into the alkaline copper solution. Duplicate samples (0.2-1.2) were assayed as described in Example 6, except that the assays were performed with alkaline copper solution containing and lacking 2% sodium dodecyl sulphate. The protein solution containing and lacking 1% Triton-X100 were used. The results are shown in the FIG. 10. Plot B shows the control experiment, and Plot D shows the experiment in which the alkaline solution contained 2% sodium dodecyl sulphate. The addition of sodium dodecyl sulphate slightly increased the colour yield. Plot A shows protein containing 1% Triton-X100 when assayed with the reagent lacking sodium dodecyl sulphate, and Plot A was distorted because of precipitation due to the presence of Triton-X100 in the protein. Plot C shows protein of Plot A assayed with the alkaline copper solution containing 2% sodium dodecyl sulphate. It is clear from the plots that the addition of sodium dodecyl sulphate counters the influence of detergent Triton-X100 and restored Plot A. Similar results have been obtained with other nonionic and cationic detergents.

EXAMPLE 9

Micro Assay System

Figure 11:
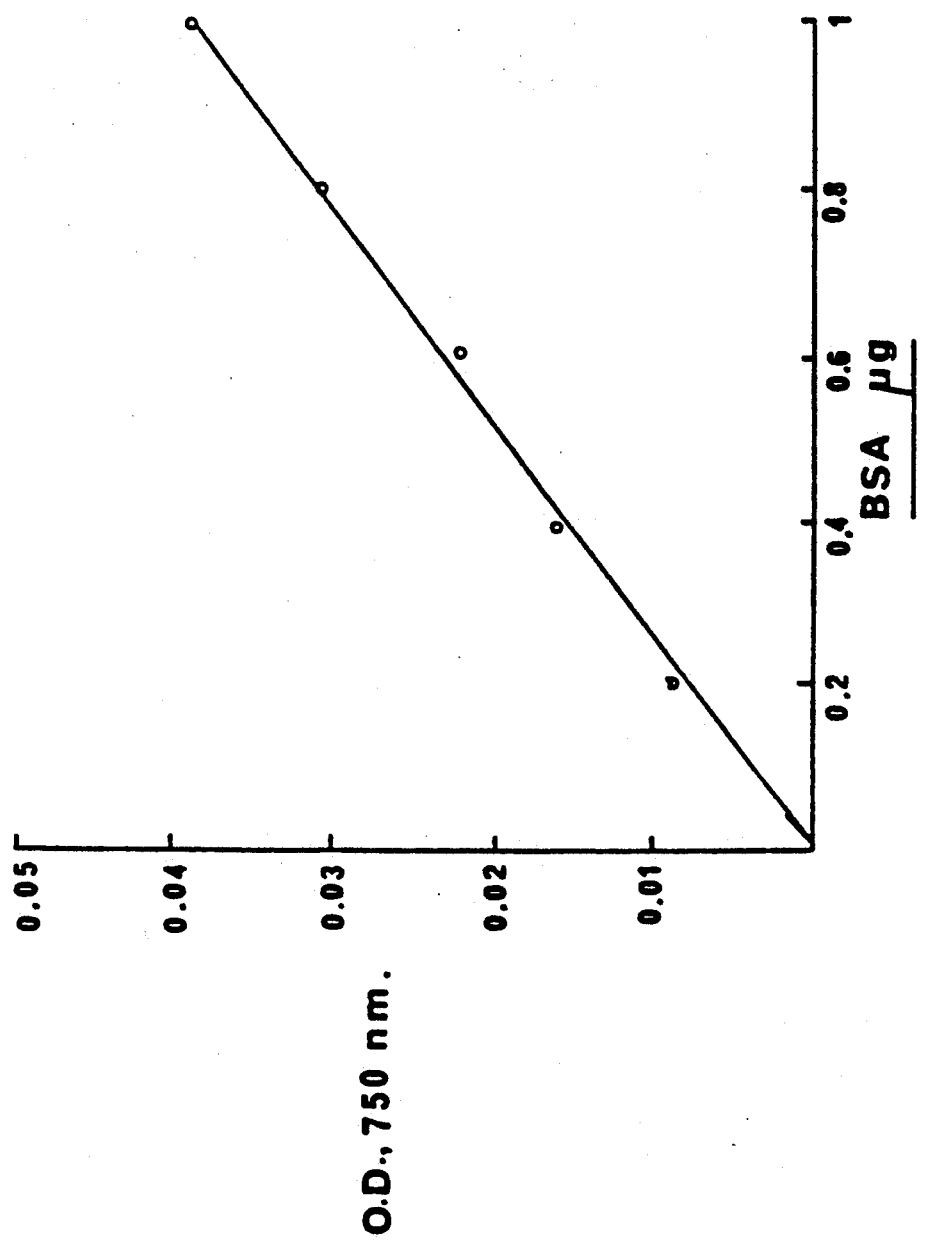

Micro protein assay was performed in either microtiter plates or micro test tubes in a total assay volume of 0.2-0.25 ml. Protein solution containing 0.2-1 $\mu$g protein in a volume of 5 $\mu$l was used. The protein samples were first treated with 25 $\mu$l of alkaline copper solution containing 1N NaOH in 5% sodium carbonate, 0.15% sodium tartrate and 0.05% copper sulphate followed by 174 $\mu$l of 5% Folin solution. The optical density was read after 10 minutes. FIG. 11 shows the results obtained for a micro assay system. It is clear from the result that the assay is capable of estimating protein as low as 0.2 micrograms in a sample.

EXAMPLE 10

Linearity of the Assay

Figure 12:
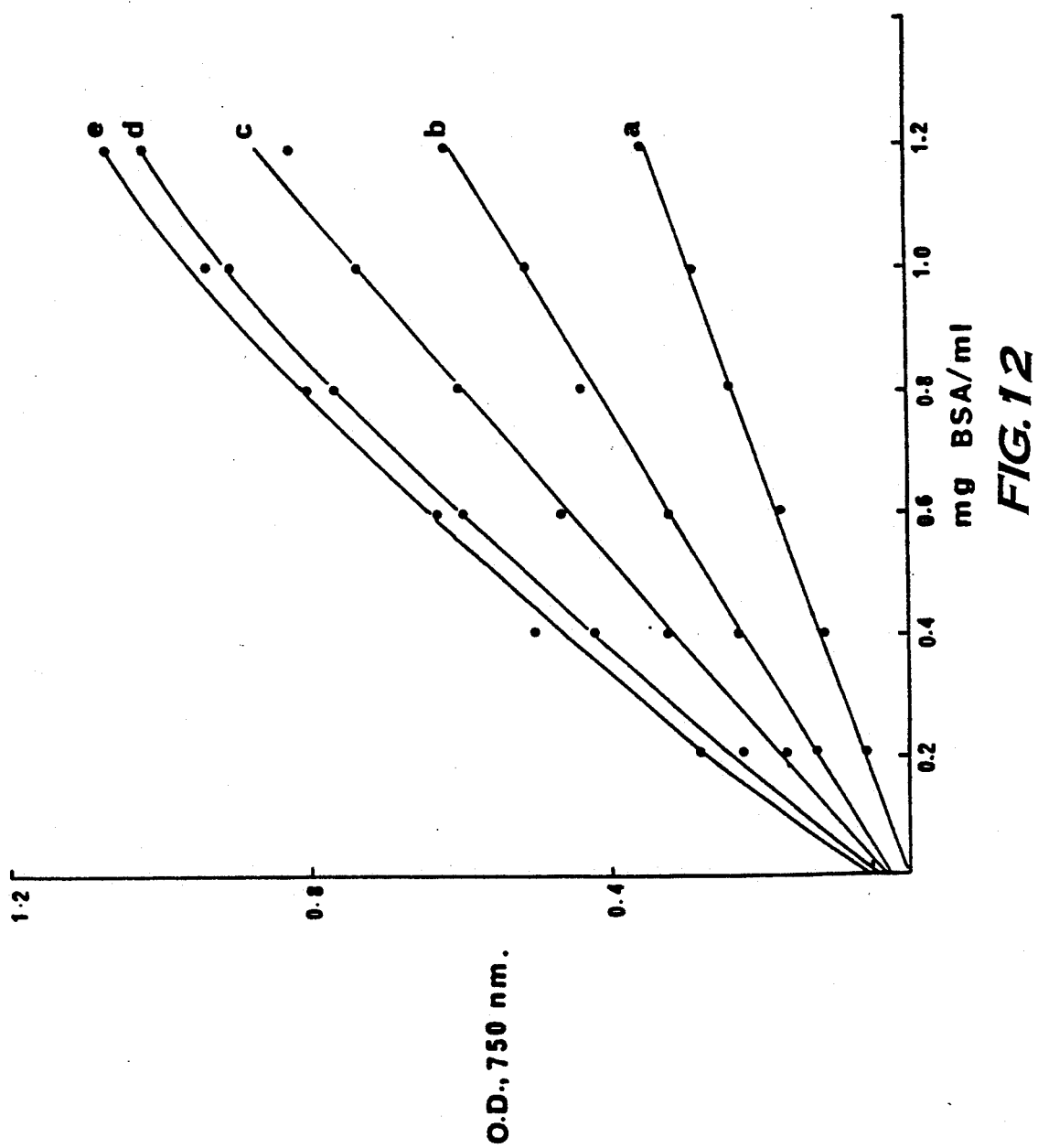

This experiment consisted of a batch of five determinations, a, b, c, d and e. Batch "a" contained 0.2-1.2 mg/ml protein in a total volume of 0.1 ml. Batches b, c, d and e contained protein 2, 3 4 and 5 times the amount of protein present in Batch a in a total volume of 0.1. The assays were performed as described in Example 6, and FIG. 12 shows the results. It is clear from the results that the assay is linear for up to 0.63-3.6 mg/ml protein per assay. Protein in excess of 0.8-4.8 mg/ml begins to lose linearity. However, it has been found that the linearity of the assay can be restored by increasing the amount of alkaline copper in the assay and correspondingly increasing the amount of Folin (result not shown).

I claim:

1. A method of assaying protein which comprises the following steps:
    (a) contacting together a protein-containing solution and an alkaline copper solution, the alkali concentration in the alkaline copper solution being from 0.2N to 2N;
    (b) contacting the product of Step (a) with Folin reagent to form an intermediate solution, the amount of Folin reagent being such that the initial pH of the intermediate solution, immediately on formation, is from 11 to 12;
    (c) allowing the intermediate solution to incubate at ambient temperature until the optical density of the intermediate solution reaches a maximum value; and
    (d) reading this maximum optical density in order to determine the amount of protein in said protein-containing solution.

2. A method according to claim 1 in which said pH in Step (b) is from 11.4 to 11.9.

3. A method according to claim 1 in which said pH in Step (b) is from 11.5 to 11.8.

4. A method according to claim 1 in which the alkaline copper solution is unbuffered in order that the pH of the intermediate solution decreases without hindrance following Step (b).

5. A method according to claim 1 in which the alkaline copper solution contains sodium or potassium tartrate.

6. A method according to claim 1 in which an anionic detergent is introduced into at least one of the solutions of Step (a) prior to Step (b).

7. A method according to claim 6 in which the anionic detergent is sodium dodecyl sulphate.

8. A method according to claim 1 in which the Folin reagent is used in a solution having a concentration of less than 2N.

9. A method according to claim 8 in which the Folin reagent is used in a solution having a concentration of 10% Folin or less.

10. A method according to claim 9 in which the Folin reagent is used in a solution having a concentration of about 5% Folin.

* * * * *